US012743847B2

(12) United States Patent
Montes et al.

(10) Patent No.: US 12,743,847 B2
(45) Date of Patent: Sep. 22, 2026

(54) SYSTEMS AND METHODS FOR GENERATING HEAD MODELS

(71) Applicant: Magnus Medical, Inc., Burlingame, CA (US)

(72) Inventors: Luis Cuenca Montes, Prescott, AZ (US); Armani Porter, Pikesville, MD (US)

(73) Assignee: Magnus Medical, Inc., Burlingame, CA (US)

( * ) Notice: Subject to any disclaimer, the term of this patent is extended or adjusted under 35 U.S.C. 154(b) by 493 days.

(21) Appl. No.: 18/497,892

(22) Filed: Oct. 30, 2023

(65) Prior Publication Data

US 2024/0144593 A1 May 2, 2024

Related U.S. Application Data

(60) Provisional application No. 63/381,414, filed on Oct. 28, 2022.

(51) Int. Cl.
*G06T 17/00* (2006.01)
*A61N 2/00* (2006.01)
(Continued)

(52) U.S. Cl.
CPC .............. *G06T 17/00* (2013.01); *A61N 2/006* (2013.01); *A61N 2/02* (2013.01); *G06T 7/11* (2017.01);
(Continued)

(58) Field of Classification Search
None
See application file for complete search history.

(56) References Cited

U.S. PATENT DOCUMENTS

2016/0228702 A1* 8/2016 Kempe .............. A61N 1/36025
2018/0365824 A1* 12/2018 Yuh ........................ A61B 6/032
(Continued)

FOREIGN PATENT DOCUMENTS

CN 110459301 A * 11/2019 ............... G06T 7/33
WO 2024092279 A2 5/2024
WO 2024092279 A3 6/2024

OTHER PUBLICATIONS

International Search Report and Written Opinion for PCT International Application No. PCT/US2023/078243, Filed Oct. 30, 2023, Search Completed Feb. 18, 2024, Mailed Mar. 25, 2024, 10 pgs.
(Continued)

*Primary Examiner* — Yi-Shan Yang
(74) *Attorney, Agent, or Firm* — KPPB LLP

(57) ABSTRACT

Described herein are systems and methods for generating a head model, e.g., a morphable head model, that may include a 3D representation of the skull and face for neurostimulation therapy. The systems and methods may generally transform a 2D image of the head of a patient into a more accurate 3D representation of the face and skull using a cylindrical scanning, skin segmentation, and/or adaptive thresholding technique. In another variation, genetic techniques, such as facial genetic morphology, may be used in conjunction with the techniques described to increase aesthetic accuracy of the 3D representation of the face and skull. Benefits of these techniques may include preservation of all facial features, reduced noise, and avoidance of foreign objects.

16 Claims, 13 Drawing Sheets
(8 of 13 Drawing Sheet(s) Filed in Color)

(51) Int. Cl.
*A61N 2/02* (2006.01)
*G06T 7/11* (2017.01)
*G06T 7/136* (2017.01)

(52) U.S. Cl.
CPC .... *G06T 7/136* (2017.01); *G06T 2207/10088* (2013.01); *G06T 2207/10132* (2013.01); *G06T 2207/20081* (2013.01); *G06T 2207/30196* (2013.01); *G06T 2210/41* (2013.01)

(56) References Cited

U.S. PATENT DOCUMENTS

| | | | | |
|---|---|---|---|---|
| 2020/0380687 | A1 | 12/2020 | Avital et al. | |
| 2021/0145608 | A1* | 5/2021 | Herr | A61B 5/004 |
| 2022/0012953 | A1 | 1/2022 | Powers | |
| 2022/0051431 | A1* | 2/2022 | Jagadeesan | G06V 10/98 |

OTHER PUBLICATIONS

Bharadwaj et al., "FLARE: Fast Learning of Animatable and Relightable Mesh Avatars", Retrieved from: https://flare.is.tue.mpg.de/, 2023, 3 pgs.

Li et al., "Learning a model of facial shape and expression from 4D scans", ACM Transactions on Graphics, 36(6) 194:1-194:17), 2017.

Madsen et al., "Probabilistic Joint Face-Skull Modelling for Facial Reconstruction", IEEE CVF Conference on Computer Vision and Pattern Recognition, Conference Jun. 18-23, 2018, Salt Lake City, Utah, DOI: 10.1109/CVPR.2018.00555.

Ossorio, "About Face: Forensic Genetic Testing for Race and Visible Traits", Journal of Law, Medicine & Ethics, 2006, 34(2), 277-292. doi:10.1111/j.1748-720X.2006.00033.x).

Schwarz et al., "Identification of Anonymous MRI Research Participants with Face-Recognition Software", The New England Journal of Medicine, vol. 381, No. 17, Oct. 24, 2019, pp. 1684-1686.

Stephan et al., "An Overview of the Latest Developments in Facial Imaging", Forensic Sciences Research, vol. 4, No. 1, Mar. 2019, pp. 10-28.

Tarassoli et al., "Facial Reconstruction: A Systematic Review of Current Image Acquisition and Processing Techniques", Frontiers in Surgery, vol. 7, Dec. 7, 2020, 61 pgs.

Kermi et al., "3D-Computerized facial reconstructions from 3D-MRI of human heads using deformable model approach", IEEE 2010 International Conference on Machine and Web Intelligence, Date of Conference Oct. 3-5, 2010, Algiers, Algeria.

* cited by examiner

SYSTEMS AND METHODS FOR GENERATING HEAD MODELS

CROSS-REFERENCE TO RELATED APPLICATIONS

This application claims priority to U.S. Provisional Application No. 63/381,414, filed on Oct. 28, 2022, which is hereby incorporated by reference in its entirety.

FIELD

This application is generally related to systems and methods for generating head models of patients undergoing neurostimulation treatment. The head models may create a more accurate and/or complete representation of the skull and face of patients, which may be helpful when the neurostimulation is used to treat a neurological or psychiatric disorder.

BACKGROUND

Transcranial Magnetic Stimulation (TMS) is a non-invasive medical procedure where strong magnetic fields are utilized to stimulate specific areas of an individual's brain to treat neurological or psychiatric disorders. When TMS is repeatedly applied in a short time frame, it is referred to as repetitive TMS (rTMS). Accelerated theta-burst stimulation (aTBS) is a patterned form of rTMS, typically administered as a triplet of stimuli with 20 ms between each stimuli in the triplet, where the triplet is repeated every 200 ms. TMS may be delivered to patients using neuronavigation systems including a neurostimulation device, such as a TMS coil, which may be positioned over a specified target location. The target location may be identified prior to treatment based on magnetic resonance imaging (MRI) of the brain of the patient. For example, neurostimulation therapies used to treat depression may often be directed to targets within the dorsolateral prefrontal cortex (DLPFC) for which there is functional anticorrelation to the subgenual anterior cingulate cortex. Such anticorrelation may be observed by various imaging modalities, including but not limited to FNIRS, doppler ultrasound, and/or fMRI.

Neuronavigation to a neurostimulation target generally requires an accurate measurement of the position and orientation of the patient's head relative to the position and orientation of the neurostimulation equipment used for treatment (e.g., the TMS coil). This measurement may be used to locate the physical position of the target on the working space (i.e., the patient's head). More specifically, the three-dimensional (3D) transform of the patient's MRI data may be aligned with the patient's head (i.e., registration) at the start of the neurostimulation procedure so that a clinician may guide the neurostimulation equipment to the specific target. This may be assisted through the use of a visual aid, such as a computer screen, or an audio aid, such as a sound, that confirms positioning over the neurostimulation target.

Current systems for neuronavigation generally include a medical or recliner type chair, one or more fiducial points and/or sensors positioned on the head of the individual, one or more distant reference points such as one or more large rack-mounted cameras or transmitters, and a TMS coil. One or more fiducial points and/or sensors may also be provided on the TMS coil. Additionally, the systems may include a neuronavigation computer configured to perform transformations to determine the placement of the coil with respect to the head. The neuronavigation computer may perform registration of the sensed position of the head of the patient obtained from the transformed data against a medical image (e.g., an MRI) or model of the individual's head, as further explained below. Given that the brain is typically the focus of TMS treatments, and thus, the acquired MRI scans, insufficient attention may be given to the patient's face. There may be regions of the face that are difficult for MRI to capture, such as the nose, resulting in facial features that are noisy, missing, or, in some cases, not adequate for visualization. Showing such an inaccurate (or incomplete) 3D representation of the MRI data to the patient could be offensive to the patient, especially if the patient has a psychiatric disorder in which they are suffering from dysmorphia.

The imaging modalities currently used for creating 3D models of a patient's head are ultrasound, Computed Tomography (CT), and MRI. Each may generate Digital Imaging and Communications in Medicine (DICOM) data sets. A DICOM data set may be referred to as a "volume" as its data is 3D, and is composed of voxels, which are like pixels in that they hold color and opacity, but also have volumetric qualities relating to width, depth, and height. Just as pixels come together to generate a two dimensional (2D) image, voxels come together to generate a 3D volume.

For example, using imaging data, software may be used to select voxels within a dataset pertaining to an anatomy of interest to generate a 3D volume, and subsequently, a model. Programs exist which allow the user to create a "segmentation" of an image. Examples of image segmentation may include: 1) Edge-Based segmentation that works by identifying the edges of objects in an image; 2) Skin segmentation, which may use thresholding (as further described below), which categorizes pixels based on their intensity compared to a given "threshold"; 3) Region-Based segmentation, which divides images into regions with similar characteristics; 4) Cluster-Based segmentation, which uses clustering algorithms (e.g., unsupervised classification algorithms) that may help identify hidden information in images; and 5) Watershed segmentation, which treats images like topographical maps with image intensities corresponding to height. When skin segmentation is used, the process may include creating an identified subset of voxels using a governing characteristic that is shared between them. One method to accomplish this task is "threshold segmentation", which segments all voxels within an identified voxel intensity. Different body tissues and materials will have different voxel intensity thresholds that capture them. This makes it possible to set a voxel intensity to capture bone, air, and soft tissue independently. However, it is often not possible to extract a complete skin segmentation of a patient's head using just one threshold (e.g., voxel intensity) since there may be areas in the MRI image that are less precise due to the nature of the MRI signal. For example, large differences in the magnetic susceptibility between the air-filled sinuses and the tissue/bone of the frontal part of the head may cause a strong and highly localized magnetic field focus in the frontal part of the head resulting in image distortion and signal drop-out near the nose. Furthermore, because signal intensity varies based on tissue type, normalizing the data is difficult because each tissue type may have a different 'baseline". Additionally, the data may contain foreign objects, such as glasses or implants. The foreign objects may result in skin segmentations that create "holes" that prevent the creation of accurate 3D representations of the patient's head. Attempts to filter or clean the MRI raw data have also failed to create accurate or complete facial features on head models.

Accordingly, it would be useful to have systems and methods that provide more accurate and pleasant 3D representations of the skull and face when neurostimulation therapy is being delivered.

SUMMARY

Described herein are systems and methods for generating head models (also referred to herein as "morphable head models") of patients undergoing neurostimulation treatment. As previously mentioned, the head models may create a more accurate (e.g., at least about 80% to about 100% accurate) and/or complete representation (e.g., a more realistic representation) of the skull and face of patients, which may be helpful when the neurostimulation is used to treat a neurological or psychiatric disorder. For example, viewing a more accurate and/or complete head model may be less disturbing to a patient having a psychiatric disorder in which they are experiencing dysmorphia. The systems and methods may transform the raw two-dimensional MRI of the head of a patient into a more accurate and/or complete 3D head model including the face and skull.

Some variations of the system for generating a head model may include instructions stored on a cloud-based server, the instructions, when executed, cause the server to obtain MRI data including two-dimensional (2D) image data of a head of a patient to a cloud-based server, the head comprising a face and a skull; generate a three-dimensional (3D) scan from the 2D image data; and combine the 3D scan and one or more 3D landmarks to reconstruct the face and skull of the patient and create a head model. The system may further include a cylindrical scanner. In some variations, the system further includes one or more cameras. In yet further variations, the system may also include one or more machine learning models such as the FLAME (Faces Learned with an Articulated Model and Expressions) model. Head models generated using FLAME may be referred to as morphable head models.

Some methods described herein for creating a head model may include transmitting MRI data including two-dimensional (2D) image data of a head of a patient to a cloud-based server, the head comprising a face and a skull; generating a three-dimensional (3D) scan from the 2D image data; detecting one or more three-dimensional (3D) landmarks; and inputting the 3D scan and 3D landmarks into a first machine learning model to reconstruct the face and skull of the patient to create the head model. The first machine learning model may be the FLAME model. The 3D scan may be generated using cylindrical scanning, and the one or more 3D landmarks may be detected using computer vision or a second machine learning model.

In some instances, a face of the 3D head models may be formed using 2D MRI data from the patient as an input using FLAME (Faces Learned with an Articulated Model and Expressions). FLAME is a lightweight and expressive generic head model learned from over 33,000 accurately aligned 3D scans. FLAME combines a linear identity shape space (trained from head scans of 3800 patients) with an articulated neck, jaw, and eyeballs, pose-dependent corrective blendshapes, and additional global expressions of blendshapes (Li et al, 2017. *ACM Transactions on Graphics*. 36(6) 194:1-194:17). A 3D scan of the 2D MRI data results in a point cloud that is input together with 3D facial landmarks on a fitting algorithm that outputs the final FLAME model (facial reconstruction). The 3D scan may be generated using a cylindrical scanning technique.

Additionally or alternatively, image segmentation may be used to create a head model. In one variation, skin segmentation may be used to create a head model. Skin segmentation is the process of creating a subset of voxels using a governing characteristic, e.g., voxel intensity, that is shared between them. For example, with respect to voxel intensity, voxels having the same intensity may be identified and grouped into a subset using a threshold segmentation process. Different body tissues will have different voxel intensity thresholds (e.g., intensity values). This makes it possible to set a voxel intensity to capture bone, air, and soft tissue independently. Described herein are methods and systems for extracting a skin segmentation from the patient's functional MRI to create an accurate 3D model of a patient's head. The methods and systems generally create a segmentation that preserves all facial features, is completely solid (without internal structures), has reduced noise and is free of foreign objects (e.g., eyeglasses, piercings). As mentioned above, generating such a skin segmentation may result in a more accurate 3D head model.

In some variations, the method for forming a 3D head model and extracting a skin segmentation of a patient's functional MRI data may be accomplished using adaptive thresholding. Adaptive thresholding may include the steps of creating a plurality of image slices of the head of the patient, where each slice of the plurality of slices represents a volume of the patient's head, determining a threshold (e.g., the voxel intensity that may result in the most desirable image) for each slice, and creating a depth map to show how much change occurs (e.g., the change in voxel intensities from the threshold). The depth map may be created using depth projections, and repeating the process until the skin segmentation is obtained. In other variations, the depth projections may be used as a guide when carving out the 3D head model from a solid volume (solid reconstruction). In these variations, brain segmentation may also be employed to compute the distance from the skull to the brain.

In other instances, ultrasound data, e.g., tissue density, may be used to determine threshold values for each segmentation of a patient's face and skull, and to construct a respective 3D model. This data may be used in conjunction with adaptive thresholding or solid reconstruction to improve skin segmentation, or may be used independently of other thresholding techniques.

BRIEF DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
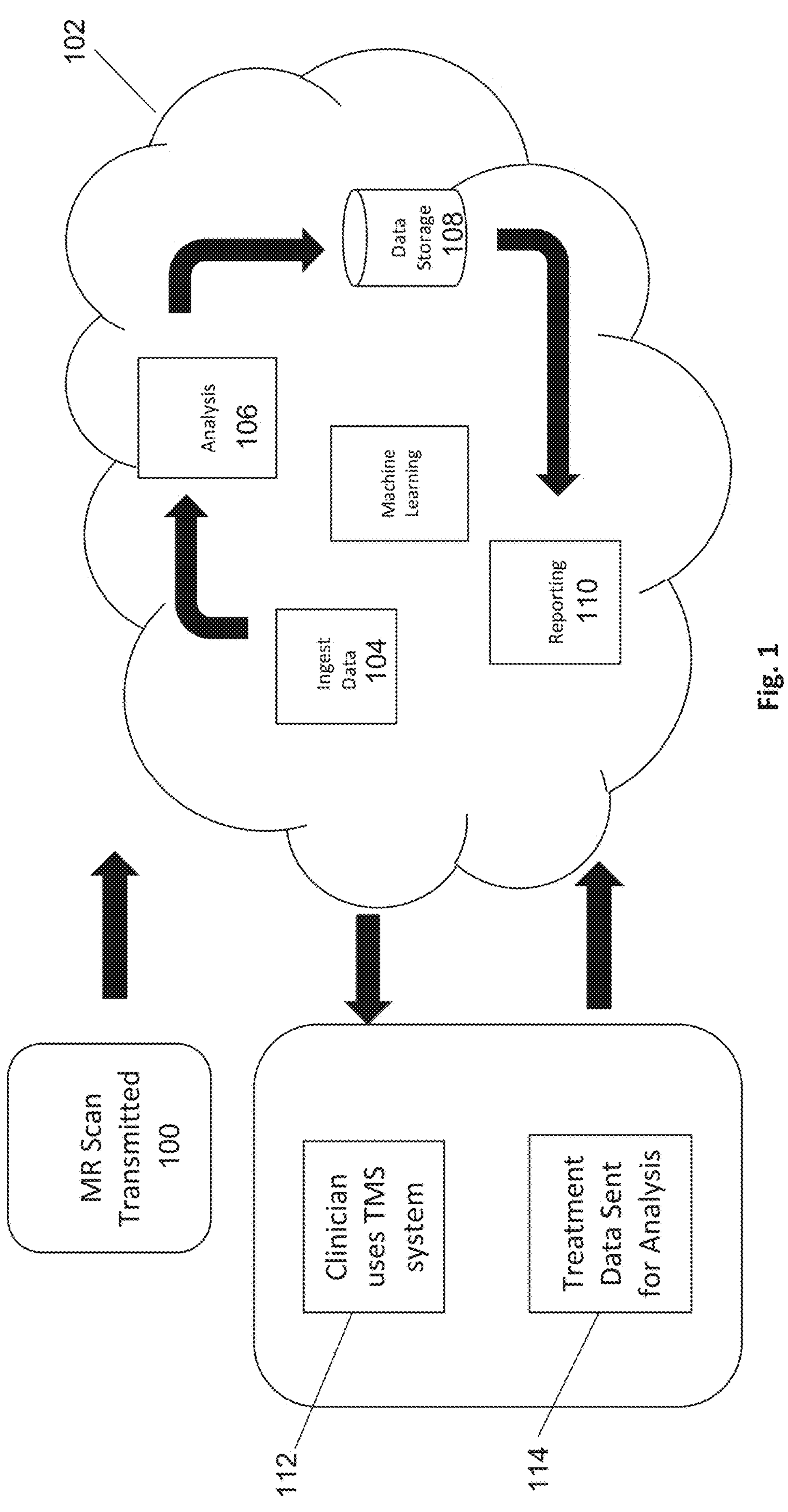
FIG. 1 is a diagram of an exemplary process for delivering TMS to a patient.

Described herein are systems and methods for generating head models of patients undergoing neurostimulation treatment. As previously mentioned, the head models may create a more accurate (e.g., about 80% to about 100% accurate) and/or complete representation (e.g., a more realistic representation) of the skull and face of patients, which may be helpful when the neurostimulation is used to treat a neurological or psychiatric disorder. For example, as previously discussed, viewing a more accurate and/or complete head model may be less disturbing to a patient experiencing dysmorphia. The systems and methods may transform the raw two-dimensional MRI of the head of a patient into a more accurate and/or complete 3D head model including the face and skull.

The psychiatric disorders that may be treated with TMS include without limitation psychiatric disorders such as depression, anxiety, post-traumatic stress disorder (PTSD), obsessive-compulsive disorder (OCD), addictions, substance use disorders, bipolar disorder, personality disorders, and schizophrenia. Psychiatric disorders, including but not limited to, depression (including major depression), substance use disorders, OCD, and personality disorders, may be associated with dysmorphia as a co-morbid disorder. The neurological disorders that may be treated with TMS include, but are not limited to, Parkinson's disease, essential tremor, stroke, epilepsy, traumatic brain injury, migraine headache, cluster headache, chronic pain, and effects of stroke.

Neurostimulation therapy, for example, transcranial magnetic stimulation (TMS), may be delivered to a neurostimulation/brain target in a patient using the head model. The head model may represent the skull and/or face of the patient with about 80% to about 100% accuracy. For example, the accuracy of the head model may represent the patient's skull and/or face with at least about 80%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100% accuracy. After generating the head model as described herein, a position of a TMS coil may be confirmed. The neurostimulation may be delivered using the TMS coil in various ways. The neurostimulation may be accelerated theta-burst stimulation (aTBS), such as accelerated intermittent theta-burst stimulation (aiTBS) or accelerated continuous theta-burst stimulation (acTBS). The neurostimulation may include applying iTBS pulse trains for multiple sessions per day over several days. In one variation, the neurostimulation may be delivered as a plurality of treatment sessions (e.g., one, two, three, four, five, six, seven, eight, nine, ten, or more than 10) on the same day for plurality of days (e.g., one, two, three, four, or five days). In some variations, the neurostimulation may be delivered for 10 sessions a day, with each session lasting 10 minutes, and an intersession interval (the interval between sessions) of 50 minutes.

The stimulation frequency of the TBS pulses may range from about 20 Hz to about 70 Hz, including all values and sub-ranges therein. For example, the stimulation frequency may be about 20 Hz, about 25 Hz, about 30 Hz, about 35 Hz, about 40 Hz, about 45 Hz, about 50 Hz, about 55 Hz, about 60 Hz, about 65 Hz, or about 70 Hz. When iTBS is used, the burst frequency (that is, the reciprocal of the period of bursting, for example if a burst occurs every 200 ms the burst frequency is 5 Hz) of the iTBS pulses may range from about 3 Hz to about 7 Hz, including all values and sub-ranges therein. For example, the burst frequency may be about 3 Hz, about 4 Hz, about 5 Hz, about 6 Hz, or about 7 Hz.

The patient may undergo multiple treatment sessions per day. In some variations, the number of treatment sessions per day may range from 2 sessions to 40 sessions. For example, the number of treatment sessions may be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40. The number of sessions for iTBS may range from 3 to 15 sessions per day. When cTBS is employed, the number of sessions may range from 10-40 sessions per day. The sessions may be performed on consecutive or non-consecutive days.

Additionally, the duration of the intersession interval may vary and range from about 25 minutes to about 120 minutes, including all values and sub-ranges therein. For example, the intersession interval may be about 25 minutes, about 30 minutes, about 35 minutes, about 40 minutes, about 45 minutes, about 50 minutes, about 55 minutes, about 60 minutes, about 65 minutes, about 70 minutes, about 75 minutes, about 80 minutes, about 85 minutes, about 90 minutes, about 95 minutes, about 100 minutes, about 105 minutes, about 110 minutes, about 115 minutes, or about 120 minutes.

In one variation, the head models described herein may be used as part of a neurostimulation treatment process, e.g., a TMS treatment process, which is provided in FIG. 1. Referring to FIG. 1, when a patient has been prescribed treatment with TMS therapy, the clinician will typically transmit the MRI scan of the head of the patient (100) to a cloud (102). The MRI data is ingested (104), analyzed, and stored and verified (108). The analysis (106) and verification (108) steps may include checking image quality and determining the scan protocol based on the indication for TMS therapy. A report may be generated (110) and transmitted to the clinician confirming image quality and providing target brain location. The report may include a visualization of the patient's head. In some instances, an accurate 3D representation of the skull and face may be included in the report. Part of the TMS therapy delivery may involve the clinician using visualization of the accurate 3D representation of the patient's head to confirm the coil placement prior to delivering TMS treatment to the patient. The TMS therapy may then be delivered (112). After delivery, the method may include sending any treatment data back to the cloud for further analysis (114).

Cylindrical Scanning

The systems and methods described herein may generally be configured to generate, e.g., using one or more processors of the system, a 3D scan from 2D image data as part of the process of creating a head model. In some variations, the systems and methods for creating a head model may be configured to transmit MRI data including two-dimensional (2D) image data of a head of a patient to a cloud-based server, where the head comprises a face and a skull, and generate a three-dimensional (3D) scan from the 2D image data using cylindrical scanning. The systems and methods may also be configured to detect, e.g., using one or more processors of the system, one or more three-dimensional (3D) landmarks, and input the 3D scan and one or more 3D landmarks into a first machine learning model, e.g., the FLAME model, to reconstruct the face and skull of the head model. Head models specifically generated using FLAME may be referred to as morphable head models. The 2D image data may include data from e.g., a CT, MRI, fMRI, or ultrasound image. The systems may further include a cylindrical scanner to create the 3D scan. In some variations, the systems may further include one or more cameras.

Figure 3:
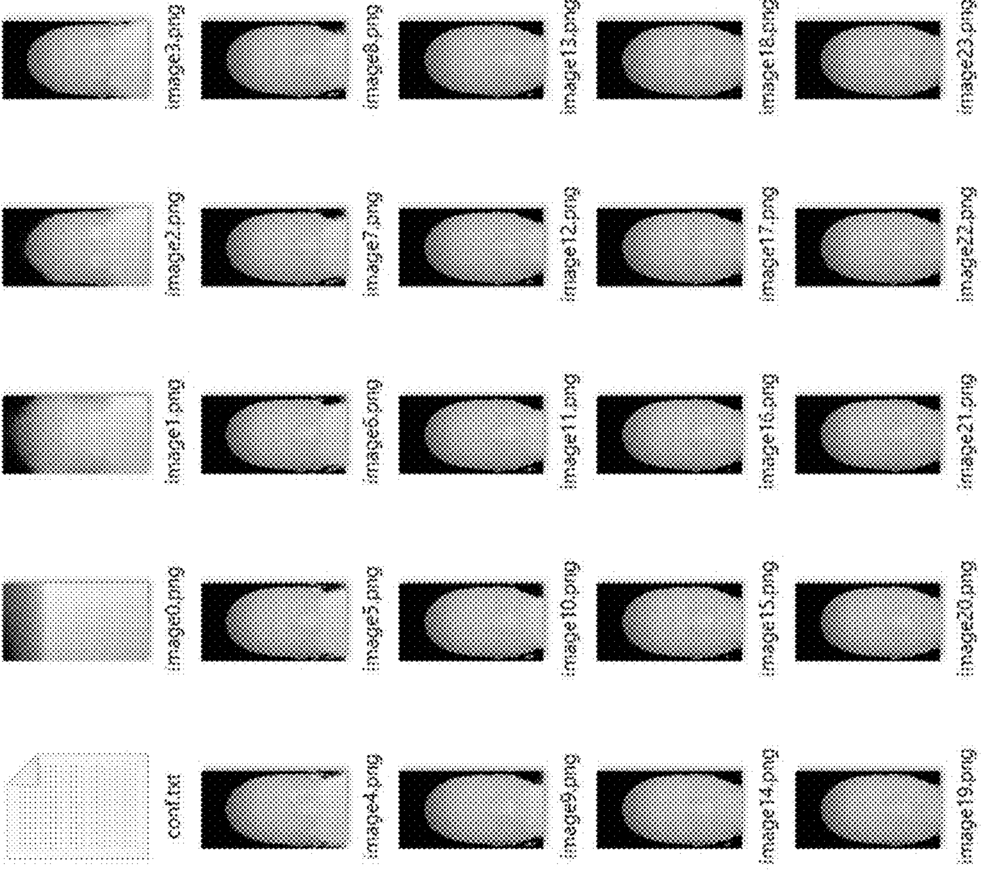
FIG. 3 depict exemplary images created by cylindrical scanning.

In some variations, cylindrical scanning may generate a 3D scan from 2D MRI data of a patient's head. The cylindrical scanning procedure generally involves repeatedly projecting rays (e.g., light rays) on the MRI space from inside a cylinder in the direction of the area of the patient's face, resulting in the creation of a point cloud. The cylindrical scan may be generated using a cylindrical scanner. The cylindrical scanner may be part of the system including the one or processors for generating the 3D scan and/or the one or more 3D landmarks, or may be a separate system that transmits the cylindrical scanning data (e.g., wirelessly or via a cable connection) to the one or more processors. Cylindrical scanning be used to create a virtual 3D scan of the face and skull that may then be used to compute a final 3D facial reconstruction. More specifically, the cylindrical scanning technique generally projects rays on the MRI space from the inside of a cylinder and in the direction of the area where the patient's face and skull are located (cylindrical projection) until an intersection of data is found, using a certain threshold. That point (intersection of data) may be considered a surface point. All of the collected points may be stored on an image using RGB channels to encode the point position creating a point cloud. A set of 30 different images based on different thresholds may then be computed (e.g., FIG. 3 is a subset). These images may be compared in batches using different buffers and sorted based on noise and consistency between buffers to find the best compound image. The resulting threshold list may be used to extract the most useful skin segmentation (filtered MRI data). The resulting points may be used to create a 3D mesh that may be used in the fitting process.

The use of landmarks may be helpful when determining the output of the 3D model fitting process. In one variation, one or more landmarks may be detected using computer vision. Computer vision may help create a realistic rendering of the data using an open source algorithm for 2D facial recognition and landmark extraction. These landmarks may then be projected on the MRI data to derive the final one or more 3D landmarks. In some variations, a machine learning model may be generated by training and testing the model using manual tagged landmarks directly on the MRI data. In other variations, the one or more 3D landmarks may be detected using genetic facial morphology. For example, genetic loci associated with facial shape may be analyzed to predict an individual's facial phenotype. Those landmarks associated with a respective facial phenotype may then be used to create a point cloud around which an individual's MRI data may be formed (Ossorio, P. (2006). *About Face: Forensic Genetic Testing for Race and Visible Traits. Journal of Law, Medicine* & *Ethics,* 34(2), 277-292. doi:10.1111/j.1748-720X.2006.00033.x). Put another way, landmarks that employ the use of genetic facial morphology may be utilized in the 3D model fitting process. One or more 3D cameras may be used in association with the FLAME model and/or genetic facial morphology to improve accuracy of the head model, and thus improve the appearance of the facial model produced.

Figure 2:
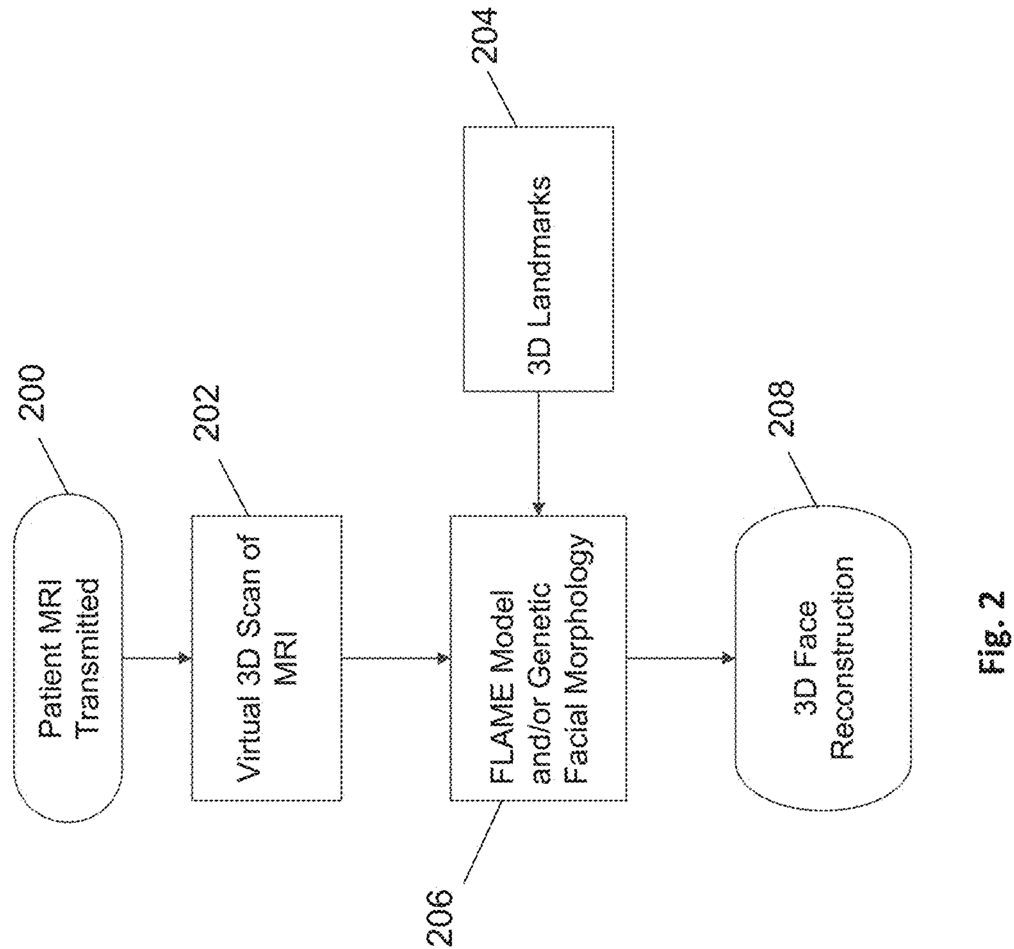
FIG. 2 is a flowchart showing an exemplary process for creating a 3D representation of the skull and face using FLAME.

In one variation, a realistic 3D facial reconstruction may be created as depicted in the flowchart provided in FIG. 2. First, in step (200) the MRI data from the head of a patient may be transmitted to the cloud (as described for FIG. 1). In step (202), a 3D scan of the 2D image may then be created using cylindrical scanning. One or more 3D landmarks may next be created in step (204) using, e.g., computer vision (as shown in FIG. 4). The 3D scan and one or more 3D landmarks may then be input in step (206) into the FLAME model to render in step (208), a realistic 3D facial reconstruction.

Figure 4C:
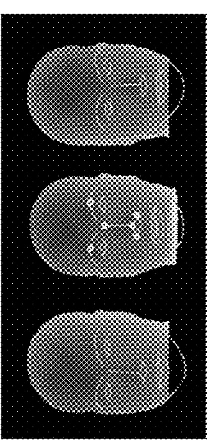
FIGS. 4A-4C depict exemplary 3D representations of the skull and face.
Figure 4B:
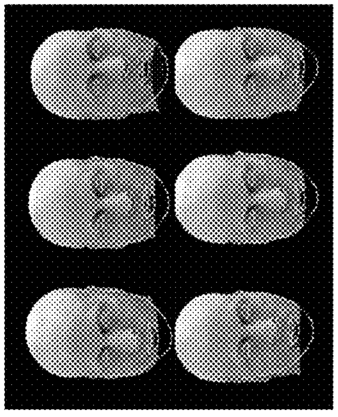
Figure 4A:
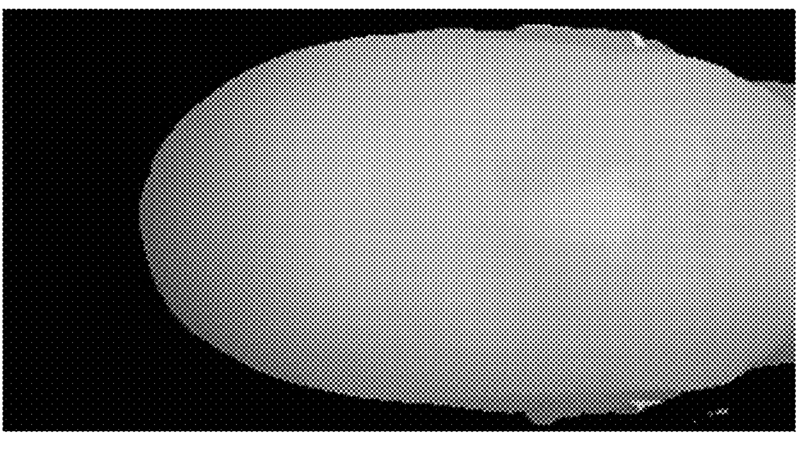

In other variations, a realistic rendering, including shadows and global illumination, of the data may be used to derive landmarks as an input to a facial recognition and 2D feature extraction algorithm using computer vision. Using different camera perspectives and averaging the output, a set of landmarks may be computed. The output may be projected on the 2D MRI scan and encoded points may be used to derive 3D points of the final landmarks. FIGS. 4A-4C illustrate an example of the computer vision process. In other variations, 3D landmarks may be computed using a machine learning model, where manually tagged landmarks on a set of MRI data may be used to train and test the model. A prediction with an accuracy of +/−2 mm (1-2 voxels) may be achieved with this method.

Figures 5A, 5B, 5C:
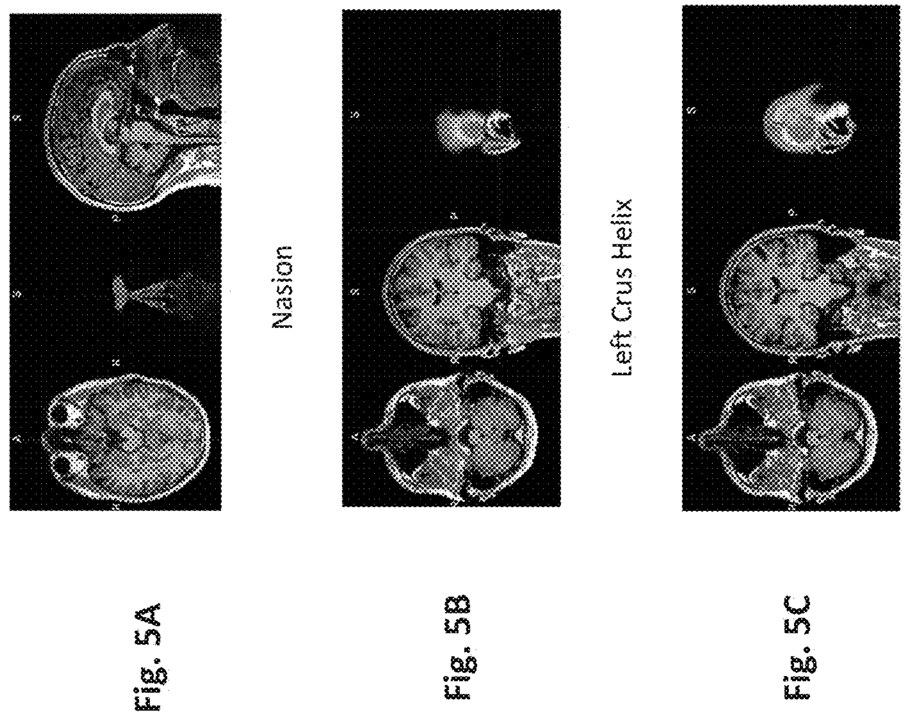
FIGS. 5A-5C depict 2D MRI images of three exemplary marked landmarks. The nasion is marked in FIG. 5A; the left crus helix is marked in FIG. 5B; and the right crus helix is marked in FIG. 5C.
Figure 6:
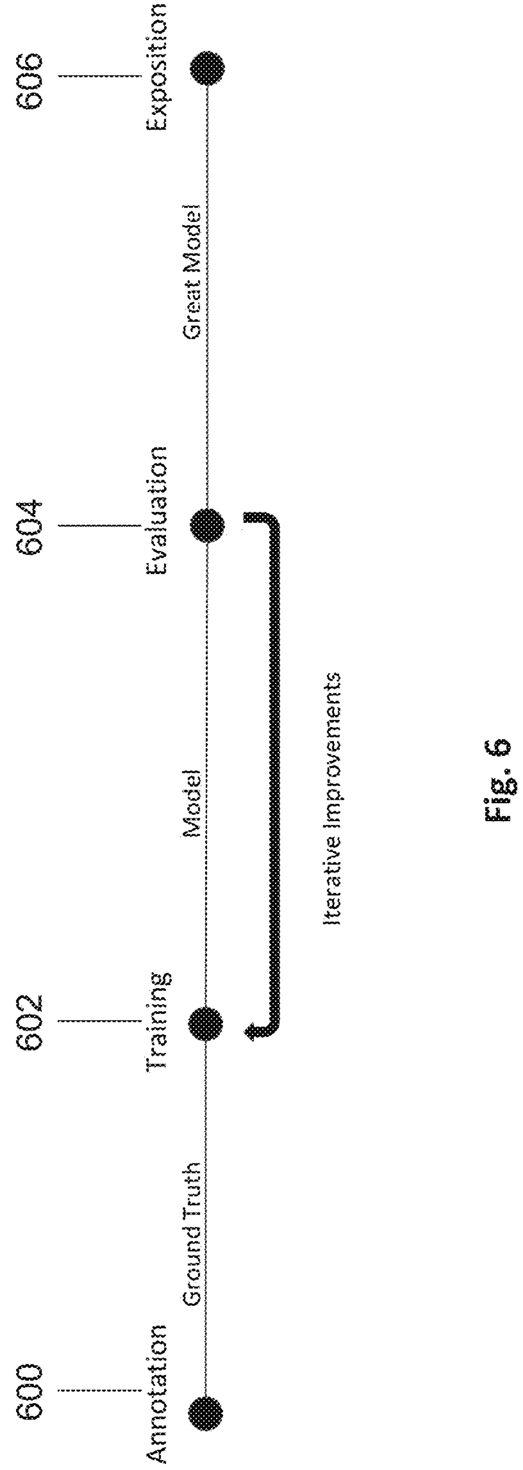
FIG. 6 is a flowchart illustrating an exemplary process for automated landmark detection.

Models for the automatic detection of one or more landmarks may also be employed in the systems and methods described herein. In some instances, and as shown in FIG. 6, development of a model to perform automatic detection of landmarks may start in step (600) with the manual annotation of three landmarks: naison, left crus of the helix, and right crus of the helix as shown on the 2D MRI scans in FIGS. 5A-5C. The annotation step (600) may generate the ground truth of the coordinates of each landmark from human expertise. The scans may be labeled to register the coordinates in voxels of the three landmarks. For example, the annotation (600) of each scan may be repeated to reduce annotator bias. Based on the manual annotation (600), it may be useful for the discrepancy between annotations to be between about 1-2 voxels. In the training step (602), a model may be trained to identify landmarks on the MRI scans. Given that it would be beneficial for the models to perform similarly on new patients (and scans) and on the scans evaluated in the training phase, an evaluation step (604) may be performed in which available scans may first be separated into two separate datasets: a training set (scans used to train the model) and a validation (or test) set (scans used to evaluate the model). Performance may then be evaluated by calculating the average distance between the predicted landmark and the ground truth positions. For example, in the case of a regression model, the performance may be calculated by taking the average mean squared error (MSE). The model performance may be assessed during two phases: training phase and post-training phase. The training phase may evaluate the validation dataset on reduced size images, thus evaluating performance as a loss. In the post training phase, the model may be replicating a true scenario or prediction and performance may be evaluated as average voxel difference. Iterative improvements may be made to improve model performance. Once a model meeting performance criterion is achieved (exposition step (606), the landmarks may be utilized in the 3D model fitting process.

Figure 7:
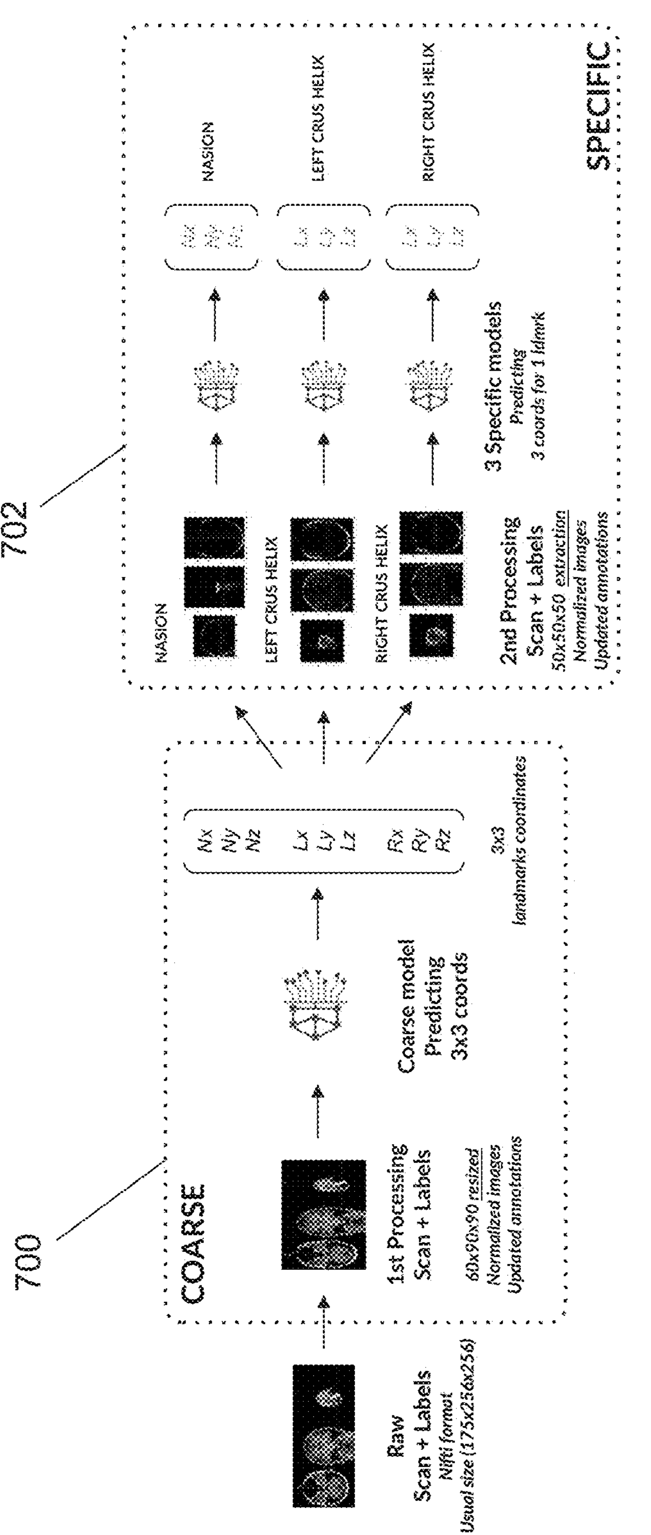
FIG. 7 provides an example of a staged model used to predict the three landmarks shown in FIGS. 5A-5C.

In another variation, the automatic detection of one or more landmarks may use a multi-phased regression model. Referring to FIG. 7, an exemplary multi-phased regression model that may be implemented is a ResNet deep neural network that predicts the 3×3 coordinates (x, y, z) of the one or more landmarks, e.g., three landmarks such as the nasion, the left crus of the helix, and the right crus of the helix), from broad to detailed resolution. The steps for the implementation of the first phase of the multiple phases may include processing of annotated scans that have been resized and normalized. The processed images may then be loaded into a course model (700) that may be configured to predict 3×3 landmark coordinates. The second phase may include a second processing step in which the annotated scans may be processed for each landmark and then loaded into three specific models configured to predict three coordinates for each of the landmarks (the nasion, the left crus of the helix, and the right crus of the helix).

Skin Segmentation

Alternatively or in addition to cylindrical scanning and inputting the data into a machine learning model, e.g., the FLAME model, skin segmentation may be used to generate, e.g., using one or more processors of the system, a 3D scan from 2D image data and a head model. More specifically, the systems and methods employing skin segmentation may be configured to transmit MRI data including 2D image data of a head of a patient to a cloud-based server, where the head comprises a face and a skull, and generate a 3D scan from the 2D image data. The 2D image data may include CT, MRI, ultrasound, or fMRI data. In some variations, it may be beneficial to use fMRI data. When a patient's MRI data is used in a segmentation process, the head model may be more accurate and/or complete, including, e.g., all facial features with reduced noise and free of foreign objects (e.g., glasses). The skin segmentation may be used for patient registration, for safe and accurate coil transformations, to measure safe and accurate brain-skin distances, as well as for use in a morphable face model (FLAME).

Figure 8:
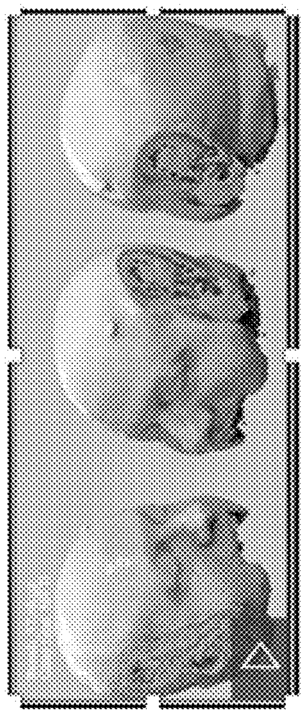
FIG. 8 is an example of a 3D head model using a single threshold to create a skin segmentation.
Figure 9:
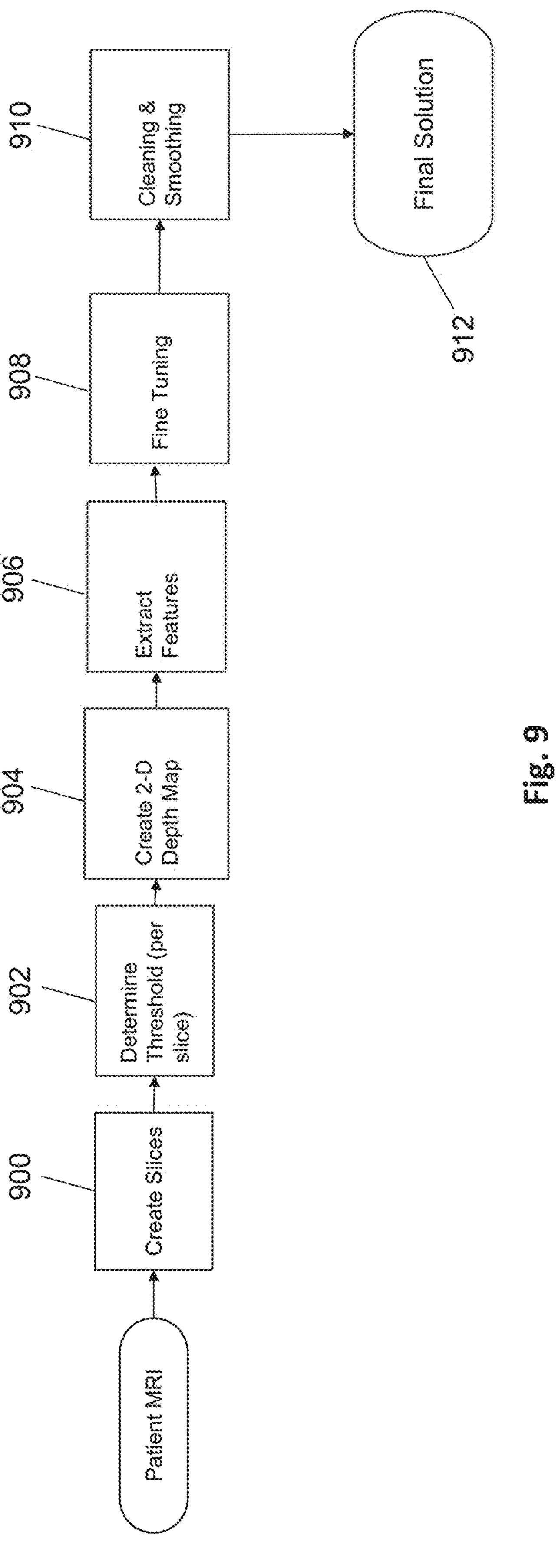
FIG. 9 is a flowchart showing an exemplary method of adaptive thresholding for skin segmentation.

In some variations, skin segmentation may generate a 3D scan from a patient's functional MRI data. As previously described, skin segmentation is the process of creating an identified subset of voxels using a governing characteristic that is shared between them. When voxel intensity is used as the governing characteristic, a process referred to as threshold segmentation may group all voxels having the same identified voxel intensity into the same segment. Different body tissues and materials generally have different voxel intensity thresholds that capture them. This makes it possible to set a voxel intensity to capture bone, air, soft tissue independently. For example, as shown in FIG. 8, a single threshold may be used to extract a complete skin segmentation of the head of a patient from the patient's fMRI data. It is generally not possible to extract a complete skin segmentation using just one threshold since each tissue type (e.g., bone, air, soft tissue) has a distinct voxel intensity. When one threshold is used, the raw data is not normalized and its precision varies from one point in space to another. The data gets more noisy and less precise as you approach the soft tissue of the nose, for example. This results in a skin segmentation that creates holes that prevent the creation of realistic 3D representations.

fMRI may also be used to create a realistic 3D facial reconstruction/head model using adaptive thresholds ("adaptive thresholding"). For example, as depicted in FIG. 9, a 3D facial reconstruction may be generated utilizing an adaptive solution that computes multiple threshold levels for different points in space. This solution may visualize data from the outside (e.g., ray tracing) so that it may minimize noise and maximize seamless transitions between adjacent data. In some variations, adaptive thresholding may be accomplished by the steps of: 1) creating one or more slices of volumes of the image (step 900); 2) determining a threshold for each slice (step 902); 3) creating a depth map using depth projections to show how change occurs (step 904); and 4) extracting features based on the depth projections (step 906). The features that may be extracted include without limitation, peaks, noise, and continuity. In general, peaks may be the number of low and high peaks of the data. This may help to filter the invalid thresholds that either result in too much noise, or that decimate the data completely. Noise may be determined by calculating the derivative of the depth map, and continuity may be the variation between adjacent cells (e.g., adjacent data points). The first estimation may still produce artifacts. To address these cases, one may use the first or basic estimation of the facial thresholds as the basis in step (908) for the fine-tuning process. A more accurate threshold computation may be performed for all projections of the image. Once a desired set of thresholds are obtained, a more accurate estimation of the data may be made. The cleaning and smoothing process in step 910 may then be performed to obtain a finalized result in step 912. Cleaning and smoothing may be based on volume blur that recreates the morphological effect of dilation and erosion.

Figure 10:
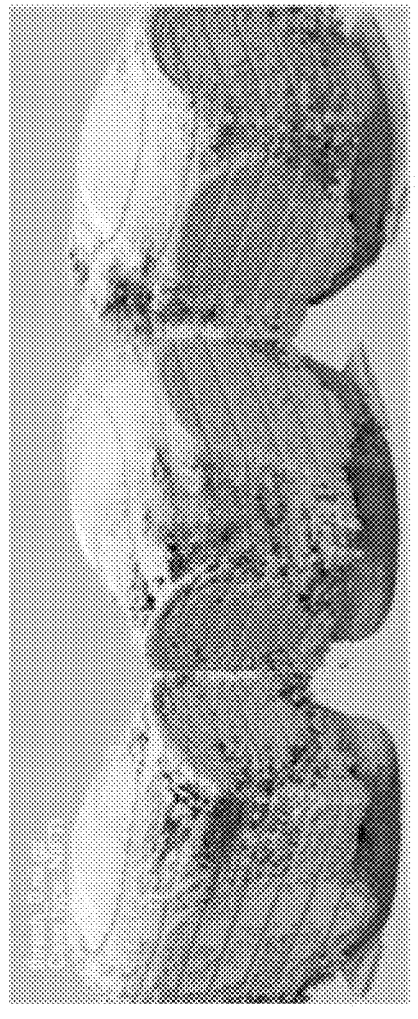
FIG. 10 depicts an example of a 3D representation of the head of a patient including volume slices.
Figure 11:
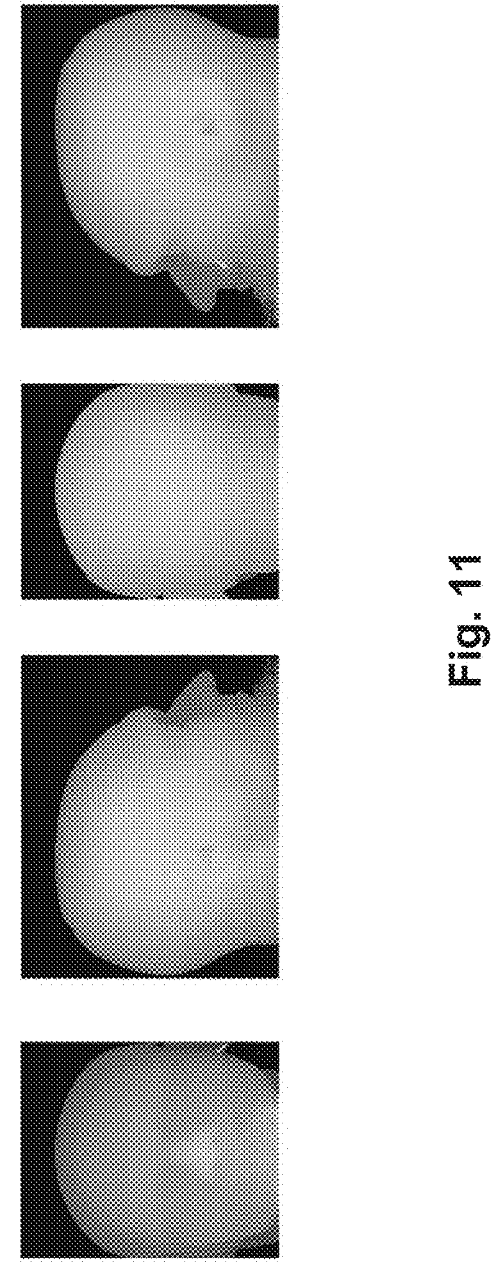
FIG. 11 depicts an example of 2D projections showing distance from a set point.
Figure 12D:
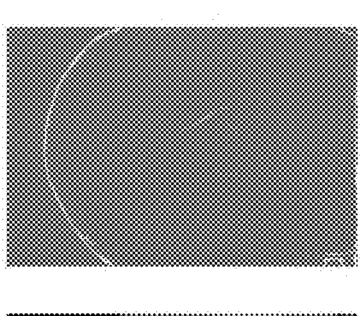
FIGS. 12A-12D are examples of the derivative of a 2D projection of an image with an incorrect segmentation (FIGS. 6A and 6B) and corrected segmentation (FIGS. 6C and 6D) image.
Figure 12C:
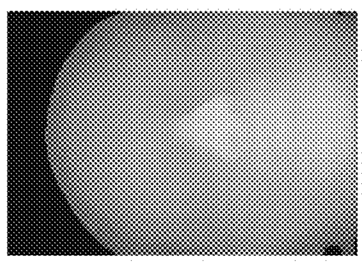
Figure 12B:
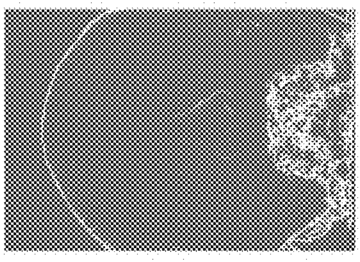
Figure 12A:
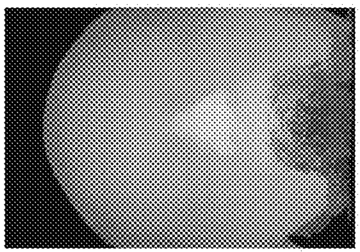

After slices of volumes of the image are created, as shown in FIG. 10, thresholds (voxel intensity) for each slice may be determined using, e.g., depth projections, as illustrated in FIG. 11. The slices and depth projections may be visualized on a display or screen of the system. Depth projections may be 2D projections of the imaging data from one side of a bounding box, where each value may correspond to the distance from the point to the first non-zero value. In some variations, it may be useful to compute the derivative of a projection. Computing the derivative of a projection may be one way to determine the amount of total noise and to quantify the smoothness of the transitions between adjacent projected points. FIGS. 12A-12D provide examples of derivatives of depth projections. FIGS. 12A and 12B show an incorrect segmentation that may result in higher derivative values. For example, the "holes" around the mouth and chin translate to noisy transitions. In contrast, FIGS. 12C and 12D illustrate a more complete segmentation that may create a smoother and seamless derivative.

Figures 13A, 13B:
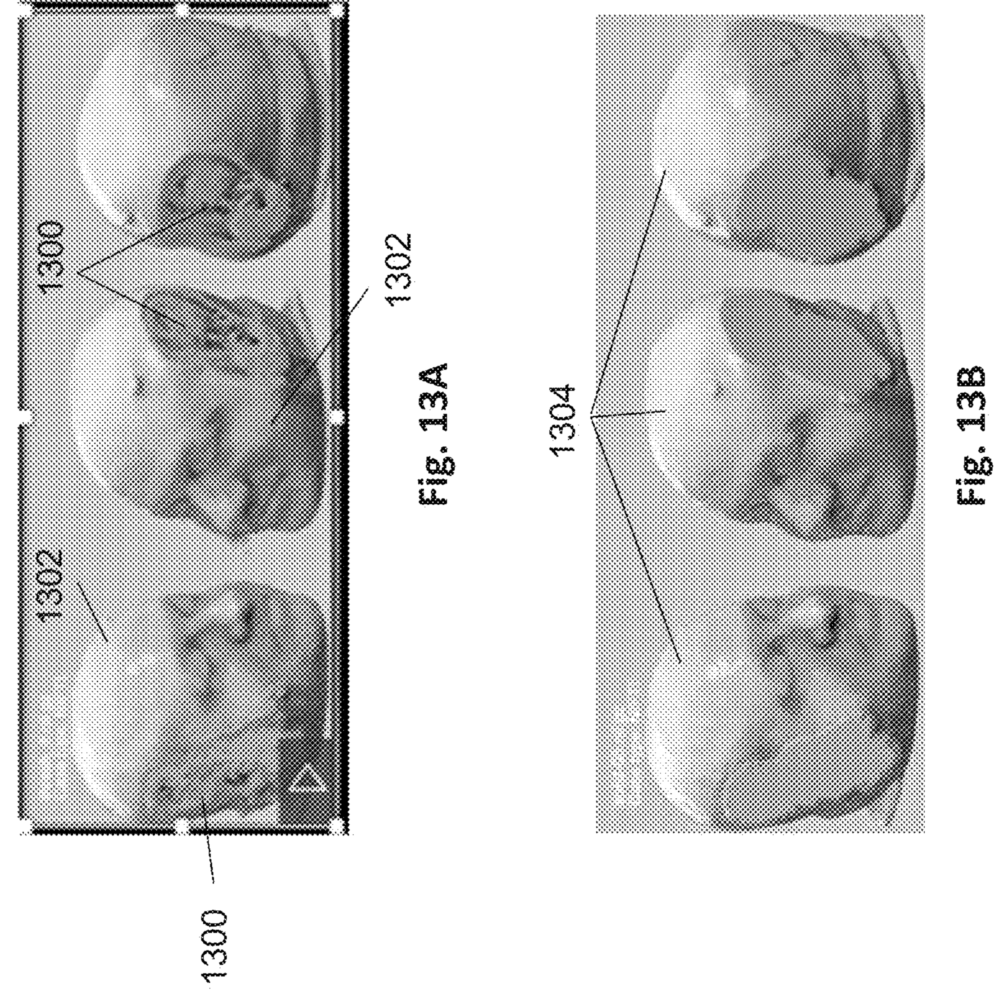
FIGS. 13A and 13B depict exemplary 3D patient head models prior to cleaning and smoothing (FIG. 13A) and after cleaning and smoothing (FIG. 13B).

Once a desired set of thresholds have been obtained through the fine-tuning process, there may still be noise or external elements present, which may be exemplified as holes (1300) on the side of the face (1302), as shown in FIG. 13A. Cleaning and smoothing may be accomplished by applying a blur (filter) to the whole volume and using the result as a mask to filter the original volume, resulting in the head model (1304) shown in FIG. 13B). The data that falls under certain thresholds may be eliminated. By applying the filter multiple times, the noise, detached elements, and small chunks of isolated data may be removed.

In another variation, solid reconstruction may be used to extract a solid skin segmentation. Here the exterior of a solid skin segmentation may be delimited by what the viewer sees when looking at the data from the outside, or by ray tracing. Likewise, the solid interior may be formed by what is not visible by the viewer. Depth projections may then be used to simulate what is seen and what is not seen from the outside view. For example, starting with a full solid volume, one may carve the exterior using the different side depth projections to obtain a binary solid volume of the patient's head/face. After the creation of the solid skin segmentation, there may still be holes in the data, particularly around the mouth. To alleviate the problem, the same side projections may be used to compute the location of the holes, and to determine which ones to fill.

In a further variation, tissue density instead of voxel intensity may be used to create subsets for skin segmentation. Ultrasound may be used to measure tissue density. This data may then be used to define thresholds for each skin segmentation. Given that imaging methods such as MRI and 3D scanning involve the use of large, cumbersome equipment, and that ultrasound is relatively cheap and easy to use, the employment of ultrasound may expand use of skin segmentation techniques to those individuals who cannot afford to visit or do not live near imaging centers.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to explain the principles of the invention and its practical applications, they thereby enable others skilled in the art to utilize the invention and various embodiments with various modifications as are suited to the particular use contemplated. It is intended that the following claims and their equivalents define the scope of the invention.

The invention claimed is:

1. A method for creating a head model comprising:

obtaining a magnetic resonance imaging (MRI) scan data of a head of a patient, where the MRI scan comprises two dimensional (2D) slices of the head of the patient, and where the head of the patient comprises a skull of the patient and a skin of the patient;

identifying the skin of the patient in the MRI scan data;

segmenting the MRI scan data based on the identified skin of the patient such that the 2D slices, when placed in order, define a 3D volume;

generating a mesh of the head of the patient based on the segmented MRI scan data;

generating a depth map of the head of the patient based on the segmented MRI scan data;

extracting a plurality of facial features of the head of the patient using the depth map;

providing the mesh of the head of the patient and the plurality of facial features of the head to a facial reconstruction mode;

obtaining a reconstruction of the head of the patient from the facial reconstruction model.

2. The method of claim 1, wherein the facial reconstruction model is a FLAME model.

3. The method of claim 1, wherein generating the mesh of the head comprises performing cylindrical scanning on the segmented MRI scan data.

4. The method of claim 1, wherein the MRI scan data comprises fMRI scan data.

5. The method of claim 1, wherein identifying skin of the patient is based on voxel intensity.

6. The method of claim 5, wherein a threshold voxel intensity is determined using adaptive thresholding.

7. The method of claim 1, wherein identifying skin of the patient is based on tissue density.

8. The method of claim 1, wherein one or more of the plurality of facial features are detected using computer vision.

9. The method of claim 1, wherein one or more of the plurality of facial features are detected using a second machine learning model.

10. The method of claim 1, further comprising checking the quality of the MRI data.

11. A non-transitory computer-readable media storing instructions that, when executed by a computer, cause the computer to:

obtain magnetic resonance imaging (MRI) scan data of a head of a patient, where the MRI scan comprises two dimensional (2D) slices of the head of the patient, and where the head of the patient comprises a skull of the patient and a skin of the patient;

identify the skin of the patient in the MRI scan data;

segment the MRI scan data based on the identified skin of the patient such that the 2D slices, when placed in order, define a 3D volume;

generate a mesh of the head of the patient based on the segmented MRI scan data;

generate a depth map of the head of the patient based on the segmented MRI scan data;

extract a plurality of facial features of the head of the patient using the depth map;

provide the mesh of the head of the patient and the plurality of facial features of the head to a facial reconstruction mode;

obtain a reconstruction of the head of the patient from the facial reconstruction model.

12. The non-transitory computer-readable media of claim 11, wherein the instructions, when executed, further cause the computer to: generate the mesh of the head using cylindrical scanning on the segmented MRI scan data.

13. The non-transitory computer-readable media of claim 11, wherein the facial reconstruction model is a FLAME model.

14. The non-transitory computer-readable media of claim 11, wherein to identify the skin of the patient, the instructions, when executed, further cause the computer to measure voxel intensity in the MRI scan data.

15. The non-transitory computer-readable media of claim 14, wherein to identify the skin of the patient, the instructions, when executed, further cause the computer to calculate an adaptive threshold for use in identifying skin based on voxel intensity.

16. The non-transitory computer-readable media of claim 11, wherein to identify the skin of the patient, the instructions, when executed, further cause the computer to measure tissue density in the MRI scan data.

* * * * *